United States Patent
Landes

(10) Patent No.: US 8,915,936 B2
(45) Date of Patent: Dec. 23, 2014

(54) DISCECTOMY INSTRUMENT

(71) Applicant: Glen Brian Landes, Quakertown, PA (US)

(72) Inventor: Glen Brian Landes, Quakertown, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 13/763,082

(22) Filed: Feb. 8, 2013

(65) Prior Publication Data
US 2013/0282013 A1 Oct. 24, 2013

Related U.S. Application Data

(63) Continuation of application No. 12/710,796, filed on Feb. 23, 2010, now Pat. No. 8,394,101.

(60) Provisional application No. 61/154,610, filed on Feb. 23, 2009.

(51) Int. Cl.
A61B 17/32 (2006.01)
A61B 17/16 (2006.01)
A61B 17/00 (2006.01)

(52) U.S. Cl.
CPC ... *A61B 17/1659* (2013.01); *A61B 2017/00261* (2013.01); *A61B 17/1617* (2013.01); *A61B 17/1671* (2013.01)
USPC .............................................. 606/167; 606/84

(58) Field of Classification Search
USPC .............. 30/164.9, 164.95; 81/177.7, 177.75, 81/177.8; 83/771–775; 403/122, 127, 131; 606/79–85, 86 R, 99, 167–180
See application file for complete search history.

(56) References Cited

U.S. PATENT DOCUMENTS

| | | | | |
|---|---|---|---|---|
| 5,015,255 | A * | 5/1991 | Kuslich | 128/898 |
| 6,830,574 | B2 * | 12/2004 | Heckele et al. | 606/104 |
| 7,988,699 | B2 * | 8/2011 | Martz et al. | 606/99 |
| 8,221,425 | B2 * | 7/2012 | Arcenio et al. | 606/84 |
| 2001/0034526 | A1 * | 10/2001 | Kuslich et al. | 606/80 |
| 2005/0049623 | A1 * | 3/2005 | Moore et al. | 606/170 |
| 2008/0183175 | A1 * | 7/2008 | Saal et al. | 606/84 |
| 2008/0243126 | A1 * | 10/2008 | Gutierrez et al. | 606/84 |

* cited by examiner

*Primary Examiner* — Nicholas Woodall
*Assistant Examiner* — Larry E Waggle, Jr.

(57) ABSTRACT

The present invention provides a discectomy instrument that is capable of removing portions of the spinal disc between adjacent vertebrae in a controlled manner that is efficient and easy to use. In an exemplary embodiment, the discectomy instrument includes a handle, a rotary scraper, a barrel, a drive shaft, an outer sleeve and a retaining clip.

17 Claims, 2 Drawing Sheets

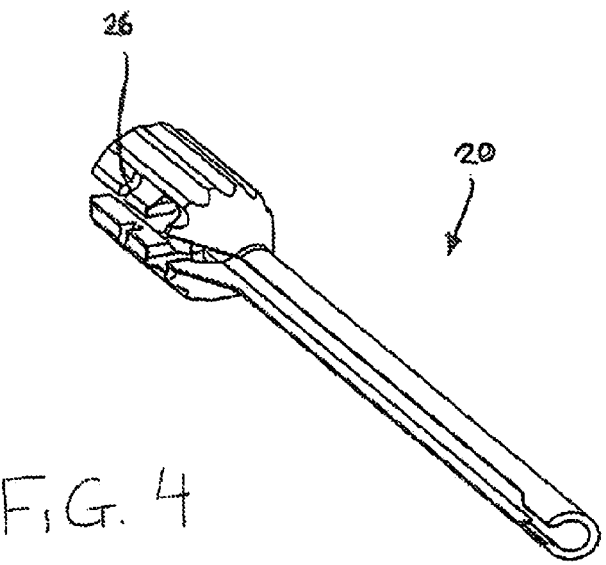
FIG. 4
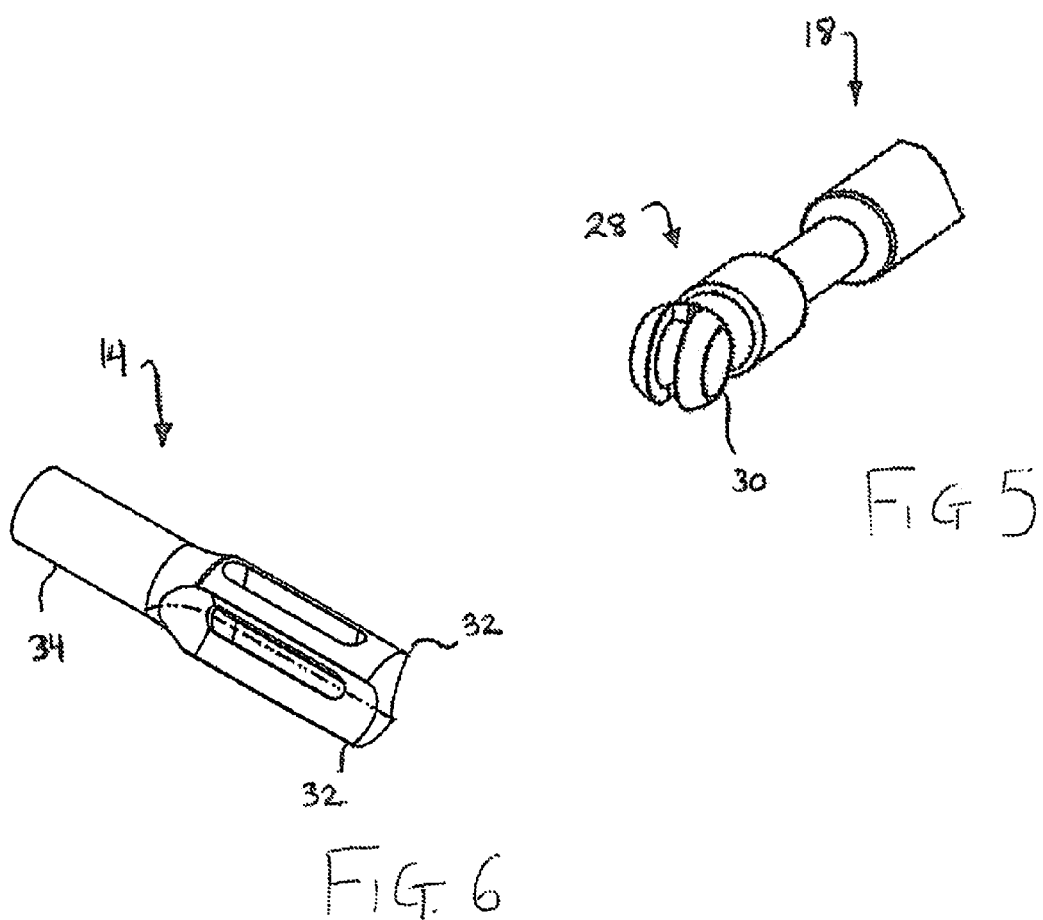
FIG 5
FIG. 6

DISCECTOMY INSTRUMENT

CROSS-REFERENCE TO RELATED APPLICATIONS

The present application is a continuation of U.S. patent application Ser. No. 12/710,796, filed on Feb. 23, 2010, which claims priority under 35 U.S.C. §119(e) to U.S. Provisional Patent Application Ser. No. 61/154,610, filed on Feb. 23, 2009. The previous application is hereby incorporated by reference in its entirety.

FIELD OF THE INVENTION

The present invention relates to an instrument for preparing the space between adjacent vertebrae to stabilize and support the spine.

BACKGROUND OF THE INVENTION

During spinal surgery, there is a need to remove portions of the spinal disc between adjacent vertebrae. Instruments are inserted into the disc space to remove portions of the disc by piercing the annulus and then the nucleus is mechanically disintegrated with the pieces being removed through suction, forceps, rongeurs, or other similar instruments.

There is a need for an instrument that allows for greater motion within the disc space to enable the nucleus to be disintegrated and removed with a minimal amount of time and ease of use for a surgeon.

SUMMARY OF THE INVENTION

In a preferred embodiment, the present invention provides a discectomy instrument that is capable of removing portions of the spinal disc between adjacent vertebrae in a controlled manner that is efficient and easy to use. The discectomy instrument preferably includes a handle, a rotary scraper, a barrel, a drive shaft, an outer sleeve and a retaining clip.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention

BRIEF DESCRIPTION OF THE DRAWINGS

The present invention will become more fully understood from the detailed description and the accompanying drawings, wherein:

FIG. 4 is a perspective view of the outer sleeve of the discectomy instrument shown in FIG. 1;

FIG. 5 is a close-up perspective view of the end of the drive shaft shown in FIG. 3; and FIG. 6 is a close-up perspective view of the end of a rotary scraper of the discectomy instrument shown in FIG. 1.

DETAILED DESCRIPTION OF THE PREFERRED EMBODIMENTS

The following description of the preferred embodiment(s) is merely exemplary in nature and is in no way intended to limit the invention, its application, or uses.

Figure 1:
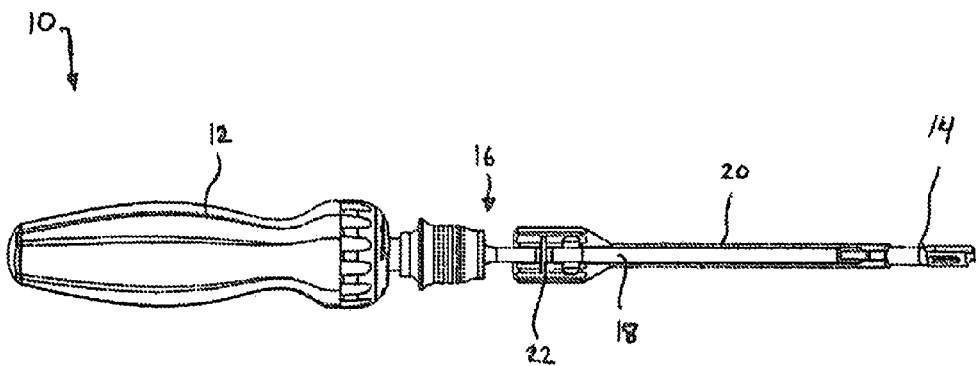
FIG. 1 is a bottom view of one embodiment of a discectomy instrument.
Figure 2:
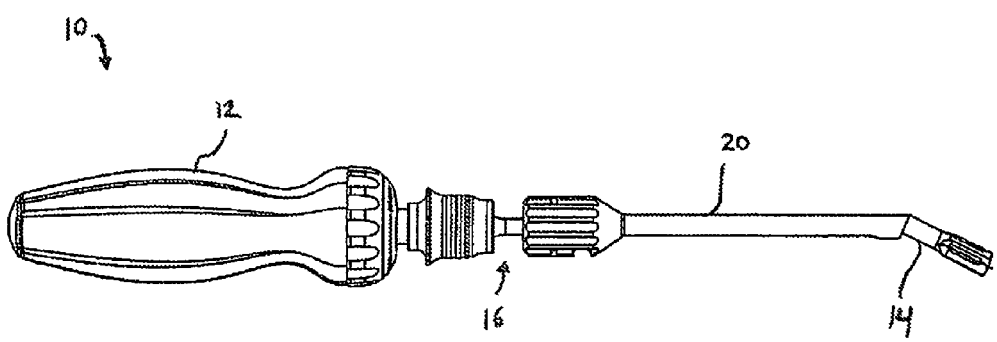
FIG. 2 is a side view of the discectomy instrument shown in FIG. 1.
Figure 3:
FIG. 3 is a side view of a drive shaft of the discectomy instrument shown in FIG. 1.

With reference to FIGS. 1 and 2, a discectomy instrument 10 according to one embodiment of the present invention is illustrated. In a preferred embodiment, the discectomy instrument includes a handle 12, a rotary scraper 14, a barrel 16, a drive shaft 18, an outer sleeve 20 and a retaining clip 22. The handle 12 is preferably connected to a medial end of the drive shaft 18 through barrel 16 via an interference fit, snap fit, or similar connection that allows torque applied to handle 12 to transmit to drive shaft 18. Barrel 16 serves as a connection means and is moveable along a longitudinal axis defined by handle 12 and drive shaft 18. When moved along the axis in a direction towards the handle 12, the barrel will disengage the drive shaft 18 from the handle 12.

Located proximate to the barrel 16, is the outer sleeve 20 which receives the drive shaft 18. In a preferred embodiment, the outer sleeve 20 has a medial end and a distal end and is connected to the drive shaft 18 via a retainer clip 20 which connects to the drive shaft 18 and outer sleeve 20 in an interference fit. Turning to FIGS. 1-4, a retainer clip receiving portion 24 can be seen on the drive shaft 18 and a retainer clip receiving slot 26 can be seen on the outer sleeve 20. The outer sleeve is connected to the drive shaft 18 in a manner as to allow the drive shaft to rotate with respect to the outer sleeve 20 but not translate with respect to the outer sleeve 20. In a preferred embodiment, the distal end of the outer sleeve 20 includes an angled edge which is configured and dimensioned to support the rotary scraper 14 in a fixed position as discussed in further detail below.

With reference now to FIGS. 1-3 and 5, in a preferred embodiment, at a distal end of the drive shaft 18 is a ball joint 28. The ball joint 28 is coupled to the rotary scraper 14 at one end and to drive shaft 18 at the other end. The ball joint 28 includes a ball member 30, a first pin which forms the major ball axis and a second smaller pin which is oriented orthogonally to the first pin and extends through the ball member 30 as well as through the first pin. The pins along with the ball member 30 engage the rotary scraper 14. With additional reference to FIG. 6, the rotary scraper 14 includes at least one, but preferably a plurality of blades 32 on one end and a receiving portion 34 on the other end. The receiving portion 34 is configured and dimensioned to engage the first and/or second pins in the ball joint 28 and rest against the ball member 30. This engagement allows the rotary scraper 14 to pivot with respect to the drive shaft 18 as well as rotate with drive shaft 18.

As mentioned earlier, with the outer sleeve 20 in place surrounding the drive shaft 18, the distal end of the sleeve 20 engages the receiving end of the rotary scraper 14. The angled end of the outer sleeve 20 allows for the rotary scraper 14 to rotate but constrains the pivoting movement of the scraper 14 to a predetermined angle. This predetermined angle is a preferred cutting angle that is designed to maximize the cutting efficiency of the rotary cutter 14 during operation of the discectomy instrument 10.

In an exemplary use of the discectomy instrument 10, after the appropriate intervertebral disc has been identified and the appropriate surgical procedures have been undertaken to create a pathway to the intervertebral disc, the discectomy instrument 10 is introduced into the pathway until the rotary scraper 14 abuts the annulus of the intervertebral disc. The annulus of the disc is then pierced using the instrument 10 or another instrument capable of accomplishing the same task. The rotary scraper 14 of the discectomy instrument 10 is then inserted into the disc nucleus. Following insertion in to the disc nucleus, torque is applied to the handle 12 which in turn transmit the torque to the rotary scraper 14 via the drive shaft 18. As the rotary scraper 14 rotates, the blades 32 cut away portions of the disc nucleus, which may be removed using forceps, rongeurs, or a suction instrument. The process is continued until the desired portion of the disc nucleus is removed.

FIGS. 1-6 illustrate the features of the present device; however, these figures alone do not encompass other possible embodiments. For example, it is contemplated that in one embodiment, the outer sleeve 20 is configured to allow the rotary scraper 14 to articulate in a controlled manner rather than being limited to a fixed angle. In another embodiment, the outer sleeve 20 may be provided with an irrigation and suction channel (not shown) for removing portions of the nucleus while still allowing the rotary scraper 14 to articulate in a controlled manner. Additionally, the rotary scraper 14 can also include a channel (not shown) that is connected to the outer sleeve 20 which allows for the suction and irrigation of the disc space. Yet in another embodiment the rotary scraper 14 can be configured so as to be detachable allowing other tools to be attached to the distal end of the drive shaft 18.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A surgical method comprising:
creating a pathway to an intervertebral disc;
introducing a discectomy instrument into the pathway, wherein the discectomy instrument includes a rotary scraper, a drive shaft operably attached to the rotary scraper, a ball joint coupled to the rotary scraper at one end and to the drive shaft at the other end, a handle and an outer sleeve, wherein the handle and the entire outer sleeve are coaxial and share a longitudinal axis;
piercing an annulus of the intervertebral disc with the discectomy instrument;
inserting the discectomy instrument into a disc nucleus of the intervertebral disc;
applying torque to the discectomy instrument to transmit a torque to the rotary scraper, thereby causing the rotary scraper to rotate and cut away portions of the disc nucleus of the intervertebral disc; and
removing the cut away portions of the disc nucleus.

2. The method of claim 1, wherein the handle is operably attached to the rotary scraper.

3. The method of claim 1, wherein the rotary scraper is configured to pivot as well as rotate with the drive shaft.

4. The method of claim 1, wherein removing the cut away portions of the disc nucleus comprises using a suction instrument.

5. A surgical method comprising:
creating a pathway to an intervertebral disc;
introducing a discectomy instrument into the pathway, wherein the discectomy instrument includes a drive shaft operably attached to a rotary scraper and a ball joint coupled to the rotary scraper, wherein the rotary scraper is configured to pivot as well as rotate with the drive shaft, wherein the discectomy instrument further comprises a handle and an outer sleeve, wherein the handle and the entire outer sleeve are coaxial and share a longitudinal axis;
inserting the discectomy instrument into a disc nucleus of the intervertebral disc;
applying torque to the discectomy instrument to transmit a torque to the rotary scraper, thereby causing the rotary scraper to rotate and cut away portions of the disc nucleus of the intervertebral disc; and
removing the cut away portions of the disc nucleus.

6. The method of claim 5, wherein the outer sleeve receives the drive shaft.

7. The method of claim 6, wherein the outer sleeve is connected to the drive shaft via a retainer clip.

8. The method of claim 7, wherein the outer sleeve is connected to the drive shaft in a manner so as to allow the drive shaft to rotate with respect to the outer sleeve but not translate with respect to the outer sleeve.

9. The method of claim 5, further comprising piercing an annulus of the intervertebral disc prior to inserting the discectomy instrument into the disc nucleus.

10. The method of claim 9, wherein the piercing of the annulus is performed by the discectomy instrument.

11. A surgical method comprising:
creating a pathway to an intervertebral disc;
introducing a discectomy instrument into the pathway, wherein the discectomy instrument includes a drive shaft operably attached to a rotary scraper, a ball joint coupled to the rotary scraper at one end and to the drive shaft at the other end, and a sleeve for receiving the drive shaft, wherein the sleeve is connected to the drive shaft via a retainer clip, wherein the discectomy instrument further comprises a handle, wherein the handle and the entire sleeve are coaxial and share a longitudinal axis;
inserting the discectomy instrument into a disc nucleus of the intervertebral disc;
using the discectomy instrument to cut away portions of the disc nucleus of the intervertebral disc; and
removing the cut away portions of the disc nucleus.

12. The method of claim 11, wherein the rotary scraper comprises a plurality of blades.

13. The method of claim 11, further comprising piercing an annulus of the intervertebral disc.

14. The method of claim 11, wherein removing portions of disc nucleus comprises using a suction instrument.

15. The method of claim 11, wherein the retaining clip engages the sleeve with the drive shaft to connect the drive shaft to the sleeve in a rotatable, non-translatable manner.

16. A surgical method comprising:
creating a pathway to an intervertebral disc;
introducing a discectomy instrument into the pathway, wherein the discectomy instrument includes a rotary scraper, a drive shall operably attached to the rotary scraper, a handle and an outer sleeve, wherein the handle and the entire outer sleeve are coaxial and share a longitudinal axis, and wherein the rotary scraper is configured to pivot as well as rotate with the drive shaft;
piercing an annulus of the intervertebral disc with the discectomy instrument;
inserting the discectomy instrument into a disc nucleus of the intervertebral disc;
applying torque to the discectomy instrument to transmit a torque to the rotary scraper, thereby causing the rotary scraper to rotate and cut away portions of the disc nucleus of the intervertebral disc; and
removing the cut away portions of the disc nucleus.

17. The method of claim 16, wherein the outer sleeve is connected to the drive shaft in a manner so as to allow the drive shaft to rotate with respect to the outer sleeve but not translate with respect to the outer sleeve.

* * * * *